(12) United States Patent
Early

(10) Patent No.: US 7,790,775 B2
(45) Date of Patent: Sep. 7, 2010

(54) PROCESS FOR USE IN GAS PHASE REACTIONS

(75) Inventor: Simon Robert Early, London (GB)

(73) Assignee: Davy Process Technology Limited, London (GB)

( * ) Notice: Subject to any disclaimer, the term of this patent is extended or adjusted under 35 U.S.C. 154(b) by 825 days.

(21) Appl. No.: 11/572,119

(22) PCT Filed: Aug. 10, 2005

(86) PCT No.: PCT/GB2005/003144

§ 371 (c)(1),
(2), (4) Date: Apr. 4, 2007

(87) PCT Pub. No.: WO2006/018610

PCT Pub. Date: Feb. 23, 2006

(65) Prior Publication Data

US 2007/0225385 A1   Sep. 27, 2007

(30) Foreign Application Priority Data

Aug. 20, 2004 (GB) ............................. 0418654.0

(51) Int. Cl.
C07C 27/06 (2006.01)
C07C 27/26 (2006.01)

(52) U.S. Cl. .................. 518/706; 518/702; 518/703; 518/704; 518/707; 568/902; 568/913

(58) Field of Classification Search .............. 518/706, 518/707, 702, 703, 704; 568/902, 913
See application file for complete search history.

(56) References Cited

U.S. PATENT DOCUMENTS

| | | |
|---|---|---|
| 1,868,096 A | 7/1932 | Dreyfus |
| 1,959,219 A | 5/1934 | Reed |
| 4,346,179 A | 8/1982 | Sugier et al. |
| 4,766,154 A | 8/1988 | Bonnell et al. |
| 5,179,129 A | 1/1993 | Studer |
| 5,216,034 A | 6/1993 | Sie |
| 5,631,302 A | 5/1997 | Konig et al. |
| 6,387,963 B1 | 5/2002 | Fitzpatrick |
| 6,433,029 B1 | 8/2002 | Fitzpatrick |

FOREIGN PATENT DOCUMENTS

DE   3518362 A1   11/1986

OTHER PUBLICATIONS

International Search Report and Written Opinion from PCT/GB2005/003144, dated Nov. 4, 2005.
Kirk-Othmer Encyclopedia of Chemical Technology, Fourth Ed., vol. 16, pp. 545-549.
International Preliminary Report on Patentability from PCT/GB2005/003144, dated Nov. 22, 2006.

*Primary Examiner*—Elvis O Price
(74) *Attorney, Agent, or Firm*—Senniger Powers LLP

(57) ABSTRACT

A process for use in equilibrium exothermic gas phase reactions comprising the steps of (a) providing a recycle stream with the addition of make-up gas, to form a feed gas stream; (b) heating the feed gas stream; (c) passing the heated feed gas stream to a first reactor containing a catalyst for the exothermic gas phase reactions at conditions suitable for the reaction; (d) removing a product stream comprising product and unreacted gases from the first reactor; (e) cooling and partially condensing the product stream to form a gas phase and a liquid phase; (f) separating the liquid phase containing the desired product from the product stream and removing said liquid phase; (g) separating the gas phase from the product stream to form a gas stream; (h) optionally mixing the gas stream from the product stream with additional make-up gas; (i) heating the gas stream; (j) passing the heated gas stream to a final reactor containing a catalyst for the exothermic gas phase reactions at conditions suitable for the reaction; (k) removing a final product stream comprising product and unreacted gases from the final reactor; (l) cooling and partially condensing the final product stream to form a final gas phase and a mal liquid phase; (m) separating the final liquid phase containing the desired product from the final product stream and removing said final liquid phase; and (n) separating the gas phase from the final product stream and recycling the gas to step (a); and in which the gas stream from step (g) is compressed prior to heating in step (i).

13 Claims, 2 Drawing Sheets

PROCESS FOR USE IN GAS PHASE REACTIONS

CROSS-REFERENCE TO RELATED APPLICATIONS

This application is based on and claims the benefit of International (PCT) Application Serial No. PCT/GB2005/003144, filed Aug. 10, 2005, which claims priority from GB 0418654.0, filed Aug. 20, 2004, both of which are herein incorporated by reference in their entirety.

The present invention relates to a process for use in equilibrium exothermic gas phase reactions, such as methanol synthesis and ammonia synthesis.

Methanol is generally produced by the conversion of synthesis gas (a mixture of carbon oxides and hydrogen) in the presence of a suitable catalyst. This conventional process for the production of methanol is described in detail in Kirk-Othmer Encyclopaedia of Chemical Technology, Fourth Edition, Volume 16 pages 545 to 549. Synthesis gas is generally obtained from a carbonaceous feedstock, usually a hydrocarbonaceous feedstock such as natural gas, usually by steam reforming.

Ammonia is generally produced from a mixture of hydrogen and nitrogen in the presence of a suitable catalyst by means of the Haber process.

As the products of these, and other exothermic gas phase reactions, are commercially important both in their own right and as starting materials for other reactions, much development has been carried out to optimise the processes for their production. For ease of reference much of the following discussion will be directed to the production of methanol. However, it will be understood that the process of the present invention is equally applicable to other reactions.

In the simplest form, a conventional process for the production of methanol comprises feed gases being preheated by heat exchange with a product stream from the reactor and then passed to a reactor containing a suitable catalyst. The product stream from the reactor is cooled by heat exchange with the incoming feed gases and then condensed against air and/or cooling water to recover crude methanol in a vapour/liquid separator. A small proportion of the unconverted feedstock and inerts from the separator overhead may be purged to control the level of inerts in the system. The remainder may be recycled to the reactor. The crude product may then be further processed. The achievable conversion of synthesis gas to methanol is limited by the equilibrium of the reaction.

This prior art process is illustrated schematically in FIG. 1 which sets out the flowsheet for a conventional methanol synthesis. In this process, make-up gas is compressed and fed into the synthesis loop in line 1 where it is mixed with recycle gas and fed in line 2 to interchanger 3 where it is heated before being fed in line 4 to the reactor 5. In the reactor a portion of the gas is converted to methanol over a methanol synthesis catalyst (not shown). The gas leaving the reactor in line 6, which will comprise unreacted feed gas, product, and water and inerts, is cooled in the interchanger 3 before being passed in line 7 to the condenser 8 where it is further cooled and condensed against air and/or cooling water in stream 9. In the condenser 8 the product methanol and water in the gas are condensed. This condensed mixture is separated in the gas/liquid separator 10 and the crude product and any water present is passed for further purification in line 11. The unreacted gas and inerts are removed from the gas/liquid separator 10 and passed in line 12 to the suction of a circulator 13. A purge may be taken prior to the circulator in line 14 to prevent the build up of inerts in the synthesis loop. The gas is then recycled in line 15 mixed with make-up gas from line 1 and passed via the interchanger 3 to the reactor 5. The process as illustrated in FIG. 1 is generally suitable for use in plants which have a capacity of from about 1,500 to about 2,500 tonnes of methanol per day.

In view of the importance of methanol and the products of other equilibrium exothermic gas phase reactions there is a desire to increase the capacity of the production process, and it has been suggested that a larger capacity system can be achieved by splitting the reactor into two or more reactors, which together with the associated equipment, operate in parallel. In this arrangement, the interchanger and condenser become multiple shells and the loops are split at the point at which the make-up gas and recycle are mixed and then recombined in the gas/liquid separator. This arrangement enables the large catalyst volume that is required to achieve the desired level of conversion to be accommodated. Thus it will be understood that placing the reactors in parallel essentially results in the use of two parallel loops with a common product separation stage.

As an alternative to these parallel arrangements it has been suggested that two or more reactors may be operated in series since this may allow for higher conversions per loop cycle to be achieved. In U.S. Pat. No. 1,868,096 a system is described in which the feed is passed to a first reactor in which a partial conversion to methanol occurs. The mixture of product and unreacted gases is cooled and partially condensed and the methanol is collected in a receiver. The remaining unreacted gases are heated and then introduced into a second reactor. This procedure continues through a series of reactors.

U.S. Pat. No. 1,959,219 describes a process for producing compounds containing carbon, hydrogen and oxygen in multiple reaction loops. A series of reactors is used in at least the first loop.

U.S. Pat. No. 4,346,179 describes an alternative process for the production of methanol from synthesis gas in two reactors. In this arrangement, unreacted gases leaving the second reactor are recycled back to the inlet of the second reactor. Similarly U.S. Pat. No. 4,766,154 describes an arrangement in which there is a two stage process and where unreacted material from the second reactor is recycled to the inlet to the second reactor to improve the efficiency of the process. The system of U.S. Pat. No. 4,766,154 is described with reference to a liquid phase reaction. A farther example of a liquid phase system can be found in U.S. Pat. No. 5,179,129.

An alternative system is described in U.S. Pat. No. 5,216,034 in which a process for the production of methanol is carried out in a multi-stage reaction system comprising multiple fluidised beds with removal of methanol between each fluidised bed. U.S. Pat. No. 5,631,302 similarly discloses product removal between series reactors.

U.S. Pat. No. 6,387,963 and U.S. Pat. No. 6,433,029 describe processes in which reactors are used in series with some or all of the make-up gases being added to second or subsequent reactors.

Whilst these processes offer some improvements over the conventional basic process for the production of methanol as illustrated in FIG. 1, they still suffer from various disadvantages and drawbacks. For example, whilst removal of product between the reactors may push the equilibrium in favour of further product formation, increased temperatures will be required to achieve acceptable reaction rates in the second and subsequent reactors which may result in an increase in the deactivation rate of the catalyst and hence a reduction in catalyst life.

A process may be proposed in which the conversion of reaction gases to product is increased combined with a reduction in the volume of catalyst utilised and in which the circulation ratio of unreacted gas in any recycle to make-up gas can be reduced. However, the higher partial pressures of the reactants in the reactors can lead to excessive reaction and high temperatures. This may be a particular problem at the beginning of life conditions for the reactor. These high temperatures may lead to a higher deactivation rate for the catalyst.

Thus, there is a need for an optimised process which will enable large volumes of the desired product to be produced in an economical manner without a reduction in catalyst life expectancy. According to the present invention there is provided a process for use in equilibrium exothermic gas phase reactions comprising the steps of:

(a) providing a recycle stream with the addition of make-up gas, to form a feed gas stream;
(b) heating the feed gas stream;
(c) passing the heated feed gas stream to a first reactor containing a catalyst for the exothermic gas phase reactions at conditions suitable for the reaction;
(d) removing a product stream comprising product and unreacted gases from the first reactor;
(e) cooling and partially condensing the product stream to form a gas phase and a liquid phase;
(f) separating the liquid phase containing the desired product from the product stream and removing said liquid phase;
(g) separating the gas phase from the product stream to form a gas stream;
(h) optionally mixing the gas stream from the product stream with additional make-up gas;
(i) heating the gas stream;
(j) passing the heated gas stream to a final reactor containing a catalyst for the endothermic gas phase reactions at conditions suitable for the reaction;
(k) removing a final product stream comprising product and unreacted gases from the final reactor;
(l) cooling and partially condensing the final product stream to form a final gas phase and a final liquid phase;
(m) separating the final liquid phase containing the desired product from the final product stream and removing said final liquid phase; and
(n) separating the gas phase from the final product stream and recycling the gas to step (a);

and in which the gas stream from step (g) is compressed prior to heating in step (i).

It has surprisingly been found that the process of the present invention enables the production of the desired product to be achieved whilst reducing the circulation rate of gases and controlling the temperatures within the reactors such that an acceptable catalyst life can be achieved. In this connection it is noted that the process of the present invention offers a reduction of around 20% in circulation rate around the reaction loop when compared with prior art arrangements in which parallel reactors are used. This has a significant benefit since the maximum size of the reaction loop is generally set by the size of compressor available. Since compressor size can be limited by actual volume flow ($m^3/h$) into the suction of the compressor, if the required circulation rate per tonne of product is reduced by 30% then a loop having a 30% greater capacity can be used within the same compressor size limit.

It is acknowledged that the saving in circulation rate is balanced against an increase in pressure drop around the loop, which is achieved when the reactors are placed in series, which will result in an increase in power requirements for the circulating compressor. However, since at least a portion of the made-up gas is added to the first reactor which is generally operating at a lower pressure, the power requirement for the make-up compressor is reduced such that the overall power requirement of the compressors is not greater than that required for a parallel reactor arrangement.

In the process of the present invention, the reduction of circulation rate of the recycled gas and hence the circulation ratio increases the partial pressure of the reactants in the reactors and hence increases the available reaction rate which in turn improves productivity. As discussed above, reduction in circulation rate in prior art arrangements resulted in increased temperatures which in turn resulted in a higher rate of catalyst deactivation. However, in the present invention, the addition of make-up gas to at least the first reactor allows the partial pressure in each reactor to be adjusted and thereby provides a level of control over the amount of reaction taking place in each reactor. This in turn allows control of the peak temperatures particularly at the beginning of life of the process and hence a reduction in deactivation which will lead to longer catalyst life with maintenance of acceptable catalyst activity for a longer period.

In one arrangement of the present invention make-up gas is added to both step (a) and step (h). The relative amount of make-up gas added in steps (a) and (h) may be adjusted during the life of the catalyst to maximise the conversion of reactants to product. In one alternative arrangement more than 50% of make-up gas is added in step (a). In a preferred arrangement more than 75%, preferably more than 80%, of make-up gas is added at step (a).

A further advantage noted for the process of the present invention is that a reduction in the amount of catalyst required may be achieved than was required in prior art systems. In particular, reductions in catalyst volume by around 30 to 40% over prior art parallel reactor systems can be achieved for the same methanol production capacity. This represents a significant cost saving both in catalyst cost and reactor cost since a reduction in catalyst volume requirements will mean that a smaller reactor may be used than can be used in the parallel systems. The use of smaller reactors offers savings in both fabrication and transport costs.

A further benefit of the arrangement of the present invention is that the flow rate through each reactor is higher than is achievable in the parallel system. This increase in flow provides improved heat removal from the catalyst and better control of the catalyst bed temperature. In addition, the reaction rate achievable is increased over that achievable in the parallel reactor system.

This increased control of temperature and the ability to apply make-up gas to the first reactor, or to adjust the split of make-up gas between the reactors, enables control over peak temperature particularly at the beginning of the life of the catalyst. This is a substantial benefit over the parallel reactor arrangement as it allows control of the reaction by controlling the levels of reactants in the reactors. Thus an additional degree of freedom in controlling the reaction, particularly at the beginning of life is achieved.

In one alternative arrangement one or more additional reactors may be included between the first reactor and the final reactor. Each additional reactor will preferably have a dedicated product separation system. In one alternative configuration, one or more additional reactors may not have a product separation system. Additional make-up gas may be added to one or more of each additional reactor. Where there is a plurality of additional reactors, make-up gas may be added to some or all of the additional reactors.

One or more of the reactors may comprise two or more reactors in parallel in conventional manner.

Any suitable type of reactor may be used for the first, final and any additional reactors. The reactors may be the same or of a different type.

An adiabatic pre-converter may be included prior to the first reactor to allow lower feed gas temperatures to be used in the first reactor and to increase conversion in this reactor. In an alternative arrangement, an adiabatic pre-converter may be included prior to some or each of the reactors present.

A purge may be included at any suitable point in the system to prevent the build up of inerts.

The process of the present invention may be used in a wide range of exothermic reactions. It is particularly suitable for use in the production of methanol or ammonia.

The catalyst used in the present invention will be selected to be appropriate for the process being carried out. The catalyst in the first and final and any additional reactors may be the same or different. The catalyst for use in methanol synthesis is preferably selected from but is not limited to copper-containing catalysts, for example reduced CuO—ZnO catalysts. Preferred catalysts are those sold under the designation Z-101 by Haldor Topsøe A/S, Denmark and under the designation 51 series by JM Catalysts. For ammonia synthesis preferred catalysts include Fe impregnated with non-reducible oxides of K, Ca, Al, Be, Ce, Si or mixtures thereof.

Any suitable reaction conditions may be used and will depend on the reaction being carried out. In general they will be similar to those known for conventional systems. However, due to the use of the make-up gas being fed to the first reactor the supply pressure would be lower than that noted in conventional systems. For methanol synthesis, the reactors may be at a pressure of between about 30 bar and about 100 bar, even more preferably about 50 bar to about 80 bar. The reaction temperature is normally between about 200° C. and about 300° C., for example between about 250° C. and about 280° C. For ammonia synthesis, the reactor is typically maintained at a pressure of up to about 200 bar. Pressures of between about 70 bar and about 200 bar are preferred and a typical pressure is about 140 bar. In ammonia synthesis temperatures of between about 230° C. and about 550° C. are typically used.

The present invention will now be described, by way of example, with reference to the accompanying figures in which.

Figure 1:
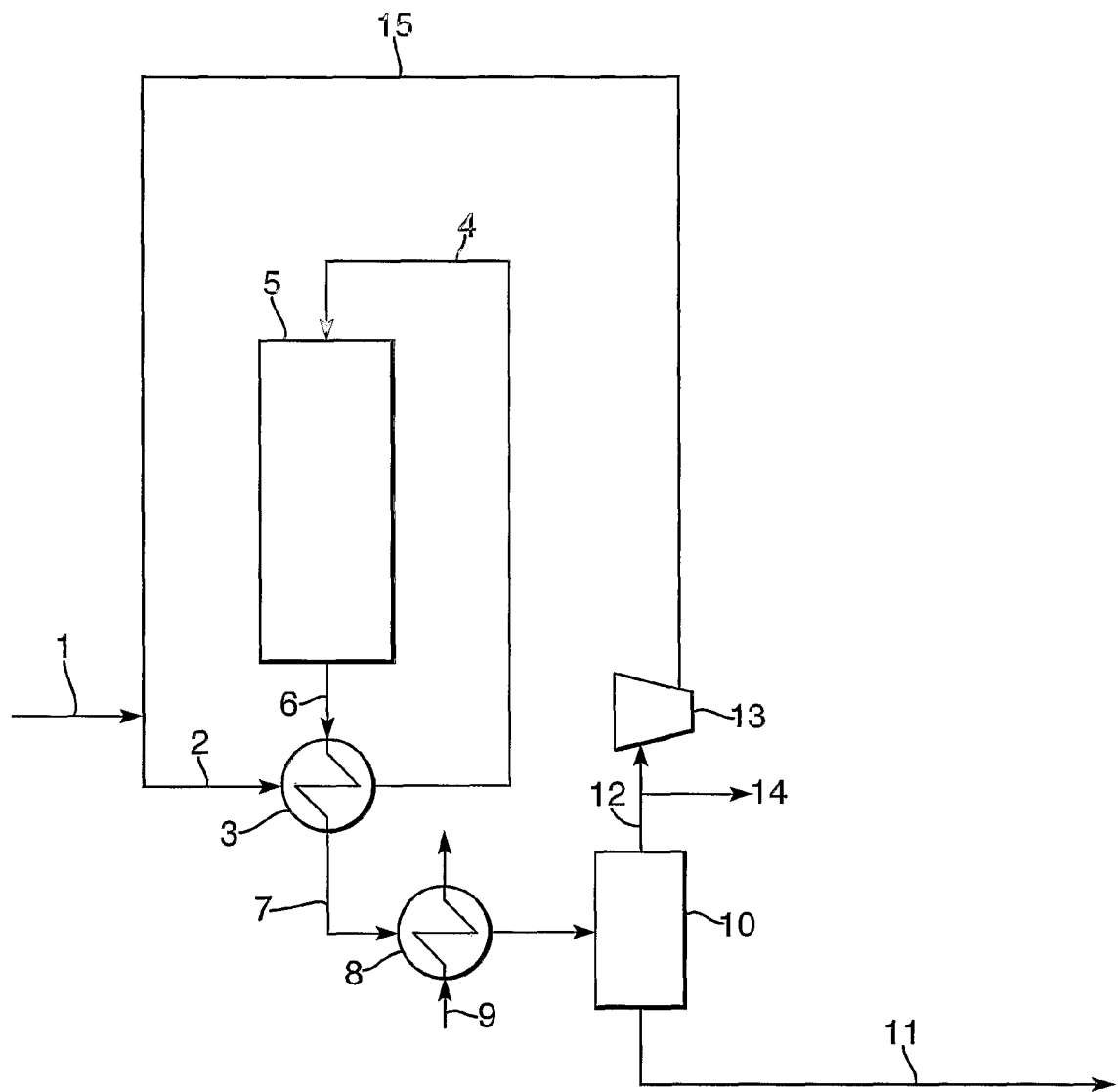
FIG. 1 is a schematic diagram of a prior art arrangement.
Figure 2:
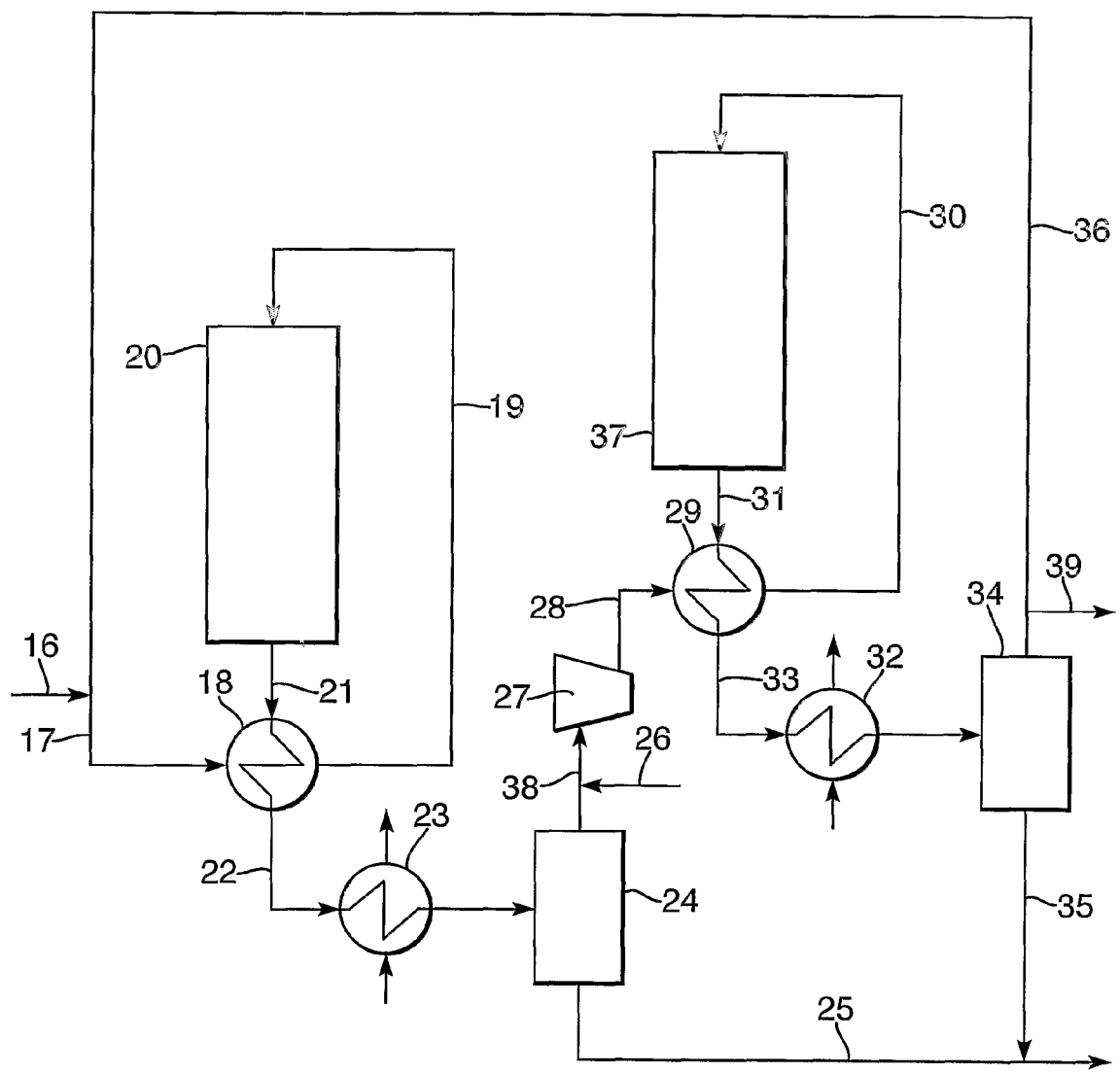
FIG. 2 is a schematic diagram of apparatus for use in the process of the present invention.

For the avoidance of doubt FIG. 2 is intended only as an aid to understanding the invention and is not intended to be construed as limiting the scope of the invention with regard to the precise arrangement of the components illustrated or the positioning thereof, the shape of the reactor vessel or any of its ancillary features. It will be understood that the system is capable of operation in the context of a multitude of known process loops for the synthesis of ammonia or methanol or any other suitable arrangement. It will be further understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

The process will be described by way of example with reference to the production of methanol.

As illustrated in FIG. 2, make-up gas is compressed and fed into the synthesis loop in line 16 where it is mixed with recycle gas and fed in line 17 to interchanger 18 where it is heated before being fed in line 19 to the reactor 20. In the reactor some of the gas is converted to methanol over a methanol synthesis catalyst. The gas leaving the reactor in line 21 is cooled in the interchanger 18 before being passed in line 22 to the condenser 23 where it is further cooled and partially condensed against air or cooling water. In the condenser 23 the product methanol and water in the gas are condensed. This condensed mixture is separated in the gas/liquid separator 24 and the crude product and any water present is passed for further purification in line 25.

The gas is removed from the gas/liquid separator 24 and optionally mixed with make-up gas added in line 26 and passed in line 38 to the suction of a circulator 27. This gas leaves the circulator 27 in line 28 and is heated in the final interchanger 29 against gas from the final reactor 37. The heated gas is then passed in line 30 to the final reactor 37 where at least some of the unreacted gas is converted to methanol over a methanol synthesis catalyst. The gas leaving the final reactor in line 31 is cooled in the interchanger 29 before being passed to the condenser 32 in line 33 where it is further cooled and partially condensed. This condensed mixture of water and methanol is separated in the gas/liquid separator 34 and the crude product and any water present is passed for further purification in line 35 where it is preferably combined with the methanol/water mixture in line 25.

The gas from the gas/liquid separator 34 is recycled ill line 36 where it may be mixed with make-up gas in line 16 before being heated and returned to the first reactor 20. A purge may be taken from the recycle stream in line 39 to prevent the build up of inerts in the loop.

At the beginning of life of the process, make-up gas is diverted to the final reactor 37 and is introduced in line 26 to allow control of the reaction and the peak and operating temperature in the reactors 20 and 37.

The present invention will now be further exemplified by reference to the data for Example 1 and Comparative Example 1 which is set out in Table 1 in which the operating conditions for a process for producing methanol in accordance with the present invention (Example 1) is compared with a prior art arrangement (Comparative Example 1) in which parallel reactors are used.

TABLE 1

|  |  | End of Life | | Beginning Of Life | |
| --- | --- | --- | --- | --- | --- |
|  |  | Comparative Example 1 | Example 1 | Comparative Example 1 | Example 1 |
| Configuration |  |  |  |  |  |
| No. of Reactors |  | 2 | 2 | 2 | 2 |
| Time On-Line | Months | 36 | 36 | 0 | 0 |
| Product make (per reactor) | MTPD | 2500/2500 | 3023/1977 | 2500/2500 | 2687/2313 |

TABLE 1-continued

| | | End of Life | | Beginning Of Life | |
| | | Comparative Example 1 | Example 1 | Comparative Example 1 | Example 1 |
|---|---|---|---|---|---|
| Circulator flow (% relative to Parallel EOL) | | 100 | 77 | 109 | 78 |
| MUG to final reactor | % | — | 0 | — | 50 |
| Reactors | | | | | |
| Pressure | bara | 70 | 65/70 | 70 | 65/70 |
| T peak | °C. | 268 | 270/270 | 270 | 270/270 |
| Catalyst Volume (% relative to Parallel) | | 100 | 70 | 100 | 70 |
| Compressors/Pressure Drop | | | | | |
| Circulator Power | MW | 11 | 15 | 13 | 16 |
| Syngas Compressor Power | MW | 54 | 50 | 51 | 49 |
| Total Compressor Power | MW | 65 | 65 | 64 | 65 |
| Loop Pressure Drop | bar | 6 | 10 | 6 | 10 |

Thus it can be seen that for the same methanol production the converter catalyst volume required in the present invention and hence the reactors are all reduced in size. Similarly, the circulation flow is reduced and the loop pressure drop has increased. This has resulted in an increase in circulator power but when combined with the synthesis gas compressor reduction the same total compressor power is achieved. The peak temperature of the reactors is controlled despite the reduced circulation rate. This is particularly notable at the beginning of life when some of the make-up gas is diverted from the final reactor.

The invention claimed is:

1. A process for use in equilibrium exothermic gas phase reactions comprising the steps of:
   (a) providing a recycle stream with the addition of make-up gas, to form a feed gas stream;
   (b) heating the feed gas stream;
   (c) passing the heated feed gas stream to a first reactor containing a catalyst for the exothermic gas phase reactions at conditions suitable for the reaction;
   (d) removing a product stream comprising product and unreacted gases from the first reactor;
   (e) cooling and partially condensing the product stream to form a gas phase and a liquid phase;
   (f) separating the liquid phase containing the desired product from the product stream and removing said liquid phase;
   (g) separating the gas phase from the product stream to form a gas stream;
   (h) optionally mixing the gas stream from the product stream with additional make-up gas;
   (i) heating the gas stream;
   (j) passing the heated gas stream to a final reactor containing a catalyst for the exothermic gas phase reactions at conditions suitable for the reaction;
   (k) removing a final product stream comprising product and unreacted gases from the final reactor;
   (l) cooling and partially condensing the final product stream to form a final gas phase and a final liquid phase;
   (m) separating the final liquid phase containing the desired product from the final product stream and removing said final liquid phase; and
   (n) separating the gas phase from the final product stream and recycling the gas to step (a);
   and in which the gas stream from step (g) is compressed prior to heating in step (i).

2. A process according to claim 1 wherein make-up gas is only added in step (a).

3. A process according to claim 1 wherein make-up gas is added in both step (a) and step (h).

4. A process according to claim 3, wherein the gas stream from step (g) is compressed after the addition of make-up gas in step (h) and prior to heating in step (i).

5. A process according to claim 4 wherein the relative amount of make-up gas added in step (a) and step (h) is adjusted during the life of the catalyst to maximise the conversion to product.

6. A process according to claim 4 wherein more than 50% of make-up gas is added in step (a).

7. A process according to claim 1 wherein one or more additional reactors are included between the first and final reactors.

8. A process according to claim 7 wherein make-up gas is added to one or more additional reactors.

9. A process according to claim 7 wherein the or each additional reactor has a dedicated product separation system.

10. A process according to claim 1 wherein one or more of the reactors comprises two or more reactors in parallel.

11. A process according to claim 1 wherein an adiabatic pre-converter is included prior to the first reactor.

12. A process according to claim 1 wherein an adiabatic pre-converter is included prior to some or all of the reactors present.

13. A process according to claim 1 wherein the process is for the production of methanol or ammonia.

* * * * *